(12) United States Patent
Marnfeldt et al.

(10) Patent No.: US 10,525,253 B2
(45) Date of Patent: Jan. 7, 2020

(54) CURRENT GENERATION ARCHITECTURE FOR AN IMPLANTABLE MEDICAL DEVICE INCLUDING CONTROLLABLE SLEW RATE

(71) Applicant: Boston Scientific Neuromodulation Corporation, Valencia, CA (US)

(72) Inventors: Goran N. Marnfeldt, Valencia, CA (US); Pujitha Weerakoon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 178 days.

(21) Appl. No.: 15/696,014

(22) Filed: Sep. 5, 2017

(65) Prior Publication Data

US 2018/0104468 A1    Apr. 19, 2018

Related U.S. Application Data

(60) Provisional application No. 62/407,800, filed on Oct. 13, 2016.

(51) Int. Cl.
*A61N 1/02* (2006.01)
*A61N 1/05* (2006.01)
*A61N 1/36* (2006.01)
*H03K 5/04* (2006.01)
*H03M 1/74* (2006.01)

(52) U.S. Cl.
CPC ............. *A61N 1/025* (2013.01); *A61N 1/05* (2013.01); *A61N 1/36* (2013.01); *H03K 5/04* (2013.01); *H03M 1/74* (2013.01)

(58) Field of Classification Search
USPC ....................................................... 607/11, 72
See application file for complete search history.

(56) References Cited

U.S. PATENT DOCUMENTS 6,181,969 B1    1/2001  Gord
6,516,227 B1    2/2003  Meadows et al.
(Continued)

OTHER PUBLICATIONS

International Search Report and Written Opinion regarding corresponding PCT Application No. PCT/US2017/050301, dated Nov. 24, 2017.
(Continued)

*Primary Examiner* — Nicole F Lavert
*Assistant Examiner* — Nicole F Johnson
(74) *Attorney, Agent, or Firm* — Lewis & Reese, PLLC

(57) ABSTRACT

Digital-to-analog converter (master DAC) circuitry is disclosed that is programmable to set a controlled slew rate for pulses that are otherwise defined as having sharp amplitude transitions. For example, when producing a biphasic pulse, the constant amplitude and duration of first and second pulses phases can be defined and provided to the DAC in traditional fashion. Slew rate control signals control a slew rate DAC within the master DAC, which prescribes a slew rate that will appear at sharp transitions of the defined biphasic pulses, i.e., at the beginning of the first phase, at the transition from the first to the second phase, and at the end of the second phase. The slew rate can vary with the duration or frequency of the pulses, with lower slew rates used with longer durations and/or lower frequencies, and with higher slew rates used with shorter durations and/or higher frequencies.

20 Claims, 11 Drawing Sheets

(56) References Cited

U.S. PATENT DOCUMENTS

| | | |
|---|---|---|
| 6,553,263 B1 | 4/2003 | Meadows et al. |
| 7,127,298 B1 | 10/2006 | He et al. |
| 7,177,698 B2 | 2/2007 | Klosterman et al. |
| 7,444,181 B2 | 10/2008 | Shi et al. |
| 7,539,538 B2 | 5/2009 | Parramon et al. |
| 7,623,916 B2 | 11/2009 | Julian |
| 7,801,600 B1 | 9/2010 | Carbunaru et al. |
| 7,801,602 B2 | 9/2010 | McClure et al. |
| 7,872,884 B2 | 1/2011 | Parramon et al. |
| 7,881,803 B2 | 2/2011 | Parramon et al. |
| 7,890,182 B2 | 2/2011 | Parramon et al. |
| 8,606,362 B2 | 12/2013 | He et al. |
| 8,620,436 B2 | 12/2013 | Parramon et al. |
| 8,649,858 B2 | 2/2014 | Griffith et al. |
| 8,768,453 B2 | 7/2014 | Parramon et al. |
| 9,002,465 B2 | 4/2015 | Ranu |
| 9,008,790 B2 | 4/2015 | Griffith et al. |
| 9,037,241 B2 | 5/2015 | Lamont et al. |
| 9,061,140 B2 | 6/2015 | Shi et al. |
| 9,155,891 B2 | 10/2015 | Archer |
| 9,174,051 B2 | 11/2015 | Marnfeldt et al. |
| 9,220,901 B2 | 12/2015 | Gururaj et al. |
| 9,233,254 B2 | 1/2016 | Nimmagadda et al. |
| 9,259,574 B2 | 2/2016 | Aghassian et al. |
| 9,308,373 B2 | 4/2016 | Lee |
| 9,314,632 B2 | 4/2016 | Marnfeldt et al. |
| 9,327,135 B2 | 5/2016 | Vansickle et al. |
| 9,352,162 B2 | 5/2016 | Lamont et al. |
| 9,397,639 B2 | 7/2016 | Feldman et al. |
| 2005/0245978 A1* | 11/2005 | Varrichio ............... H02M 3/07 607/11 |
| 2006/0173493 A1 | 8/2006 | Armstrong et al. |
| 2010/0268309 A1 | 10/2010 | Parramon et al. |
| 2012/0095529 A1 | 4/2012 | Parramon et al. |
| 2013/0184794 A1 | 7/2013 | Feldman et al. |
| 2015/0134029 A1 | 5/2015 | Ozawa et al. |
| 2015/0144183 A1 | 5/2015 | Yang et al. |
| 2015/0157861 A1 | 6/2015 | Aghassian |
| 2016/0051825 A1 | 2/2016 | Ter-Petrosyan et al. |
| 2016/0144183 A1 | 5/2016 | Marnfeldt |

OTHER PUBLICATIONS

U.S. Appl. No. 62/386,000, filed Sep. 10, 2016, Weiss et al.
U.S. Appl. No. 62/393,003, filed Sep. 10, 2016, Weerakoon et al.

* cited by examiner

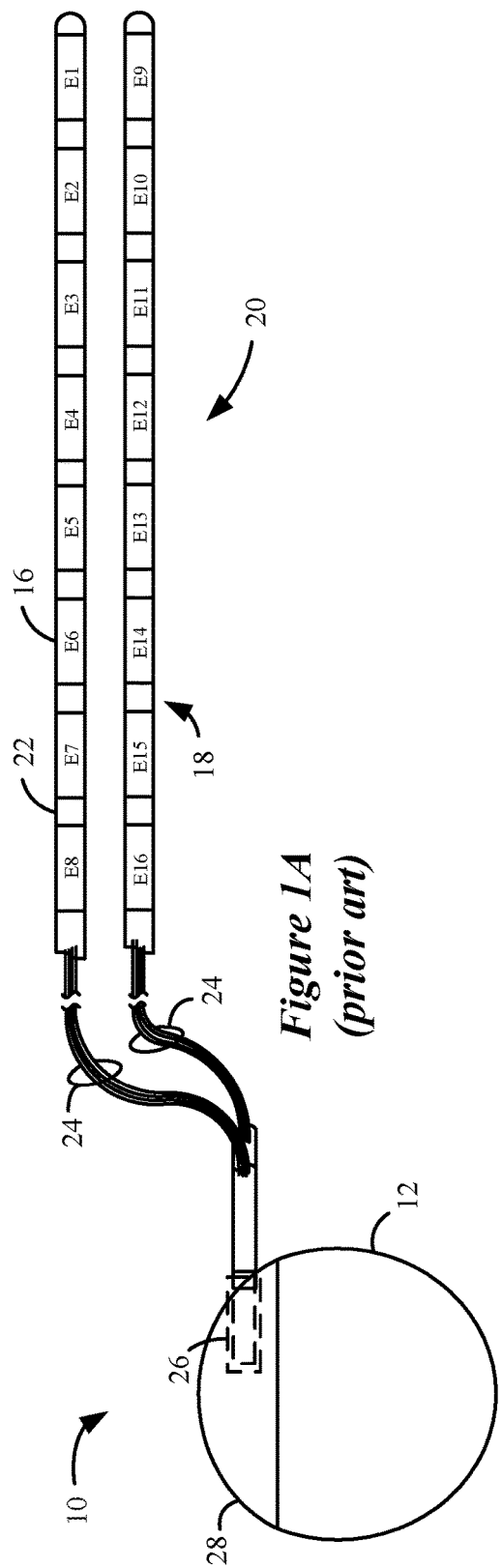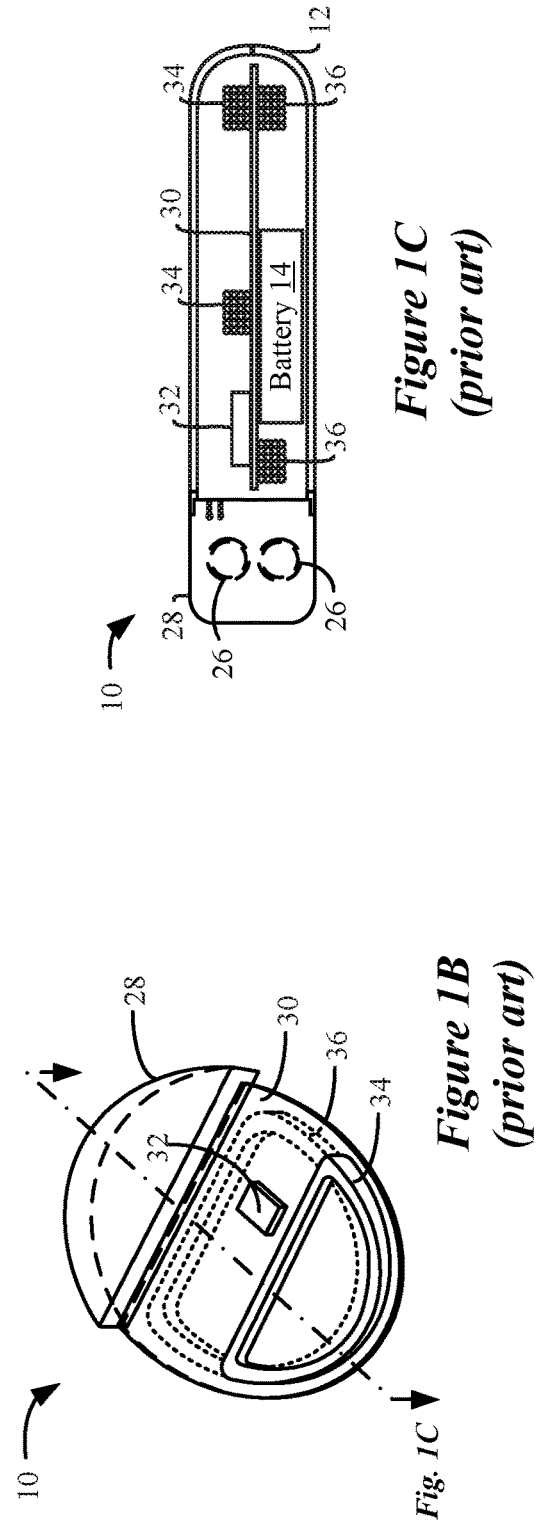
Figure 1A (prior art)
Figure 1B (prior art)
Figure 1C (prior art)

CURRENT GENERATION ARCHITECTURE FOR AN IMPLANTABLE MEDICAL DEVICE INCLUDING CONTROLLABLE SLEW RATE

CROSS REFERENCE TO RELATED APPLICATIONS

This is a non-provisional application based on U.S. Provisional Patent Application Ser. No. 62/407,800, filed Oct. 13, 2016, which is incorporated by reference in its entirety, and to which priority is claimed.

FIELD OF THE INVENTION

The present invention relates generally to implantable medical devices, and more particularly to improved current generation architectures for an implantable pulse generator.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system, including a Deep Brain Stimulation (DBS) system.

As shown in FIGS. 1A-1C, an SCS system typically includes an Implantable Pulse Generator (IPG) 10 (Implantable Medical Device (IMD) 10 more generally), which includes a biocompatible device case 12 formed of a conductive material such as titanium for example. The case 12 typically holds the circuitry and power source (e.g., battery) 14 (FIG. 1C) necessary for the IPG 10 to function, although IPGs can also be powered via external RF energy and without a battery. The IPG 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ex) on two leads 18 for a total of sixteen electrodes 16, although the number of leads and electrodes is application specific and therefore can vary. The leads 18 couple to the IPG 10 using lead connectors 26, which are fixed in a non-conductive header material 28, which can comprise an epoxy for example.

As shown in the cross-section of FIG. 1C, the IPG 10 typically includes a printed circuit board (PCB) 30, along with various electronic components 32 mounted to the PCB 30, some of which are discussed subsequently. Two coils (more generally, antennas) are shown in the IPG 10: a telemetry coil 34 used to transmit/receive data to/from an external controller (not shown); and a charging coil 36 for charging or recharging the IPG's battery 14 using an external charger (not shown). FIG. 1B shows these aspects in perspective with the case 12 removed for easier viewing. Telemetry coil 34 may alternatively comprise a short range RF antenna for wirelessly communicating in accordance with a short-range RF standard such as Bluetooth, WiFi, MICS, Zigbee, etc., as described in U.S. Patent Application Publication 2016/0051825.

FIGS. 2A and 2B show an architecture 140 for the circuitry in IPG 10, which is disclosed in U.S. Provisional Patent Application Ser. Nos. 62/386,000 and 62/393,003, filed Sep. 10, 2016, which are incorporated by reference in their entireties. Architecture 140 includes at least one Application Specific Integrated Circuit (ASIC) 160. ASIC 160 includes a microcontroller block 150, which as shown in FIG. 2B can communicate with other functional blocks in the ASIC 160 via internal bus 192. Because ASIC 160 includes an internal microcontroller 150, an external microcontroller can be dispensed with in the improved architecture 140, simplifying IPG design and saving room within the interior of the case 12 and on the IPG's PCB 30 (FIG. 1C). In one example, the microcontroller block 150 can comprise circuitry from an ARM Cortex-M0+ Processor, which may be incorporated into the monolithic integrated circuit of the ASIC 160 by licensing various necessary circuits from the library that comprises that processor. ASIC 160 can comprise a monolithic integrated circuit formed on its own semiconductive substrates ("chip"), and may be contained in its own package and mounted to the IPG 10's PCB 30.

Microcontroller block 150 may receive interrupts independent of the bus 192 and its communication protocol, although interrupts may also be sent to the microcontroller block 150 via the bus 192 as well. Even though ASIC 160 includes a microcontroller block 150, the ASIC 160 may still couple to an external bus 190. This can facilitate communications between the ASIC 160 and another device, such as a memory integrated circuit (not shown) or possibly another microcontroller device that might be coupled to the bus 190 as explained in the above-incorporated '000 and '003 Applications. Bus 190 can also facilitate communication between (master) ASIC 160 and another identically-constructed (slave) ASIC 160', shown in dotted lines in FIG. 2A. Use of an additional ASIC 160' allows the number of electrodes 16 the IPG 10 supports to be doubled, for example from sixteen to thirty two, or thirty two to sixty four. Off-bus connections 54 can facilitate master/slave interaction between ASICs 160 and 160', and as explained in detail in the above-incorporated '000 and '003 Applications.

FIG. 2B shows various functional circuit blocks within ASIC 160, which are briefly described. As mentioned, ASIC 160 includes an internal bus 192 which can couple to external bus 190 and which may duplicate bus 190's signals. Note that each of the functional blocks includes interface circuitry 88 enabling communication on the internal bus 192. Interface circuitry 88 helps each block recognize when microcontroller block 150 is communicating data with addresses pertaining to that block via bus 192.

ASIC 160 contains several terminals 61 (e.g., pins, bond pads, solder bumps, etc.), such as those necessary to connect to the external bus 190, the battery 14, the coils 34, 36, external memory (not shown), etc. ASIC terminals 61 include electrode nodes 61a (E1'-E16' and Ec') which circuit nodes are also present on the PCB 30 (FIG. 1C) inside of the IPG's case 12. The electrode nodes 61a connect to the electrodes 16 (E1-E16) on the lead(s) 18 outside of the case 12 by way of DC-blocking capacitors 55. As is known, DC-blocking capacitors 55 are useful to ensure that DC current isn't inadvertently (e.g., in the event of failure of the ASIC 160's circuitry) injected into the patient's tissue, and hence provide safety to the IPG 10. Such DC-blocking capacitors 55 can be located on or in the IPG 10's PCB 30. See U.S. Patent Application Publication 2015/0157861.

Note that there is also an electrode node 61a Ec' which is connected to the case (preferably by a DC-blocking capacitor 55), thus allowing the case 12 to operate as an electrode 16 (Ec). ASIC 160 may support other numbers or types of electrode nodes/electrodes (e.g., thirty-two electrodes E1-E32 plus the case Ec).

Each of the circuit blocks in ASIC 160 performs various functions in IPG 10. Telemetry block 64 couples to the IPG telemetry coil 34, and includes transceiver circuitry for wirelessly communicating with an external device according to a telemetry protocol. Such protocol may comprise Frequency Shift Keying (FSK), Amplitude Shift Keying (ASK), or various short-range RF standards such as those mentioned above. Charging/protection block 62 couples to the IPG charging coil 38, and contains circuitry for rectifying power wirelessly received from an external charger (not shown), and for charging the battery 14 in a controlled fashion.

Analog-to-Digital (A/D) block 66 digitizes various analog signals for interpretation by the IPG 10, such as the battery voltage Vbat or voltages appearing at the electrodes, and is coupled to an analog bus 67 containing such voltages. A/D block 66 may further receive signals from sample and hold block 68, which can be used to measure such voltages, or differences between two voltages. For example, sample and hold circuitry 68 may receive voltages from two electrodes and provide a difference between them (see, e.g., VE1-VE2 in FIG. 3, discussed subsequently), which difference voltage may then be digitized at A/D block 66. Knowing the difference in voltage between two electrodes when they pass a constant current allows for a determination of the (tissue) resistance between them, which is useful for a variety of reasons.

Sample and hold block 68 may also be used to determine one or more voltage drops across the DAC circuitry 172 (see Vp and Vn in FIG. 3, explained subsequently) used to create the stimulation pulses. This is useful to setting the compliance voltage VH to be output by a compliance voltage generator block 76. Compliance voltage VH powers the DAC circuitry 172, and the measured voltage drops can be used to ensure that the compliance voltage VH produced is optimal for the stimulation current to be provided—i.e., VH is not too low to be unable to produce the current required for the stimulation, nor too high so as to waste power in the IPG 10. Measuring Vp and Vn to determine whether VH is too high or too low is particularly useful because the resistance Rt of the patient's tissue may not be known in advance, or may change over time. Thus, the voltage drop across the tissue, Vrt, may change as well, and monitoring Vp and Vn provides an indication of such changes, and hence whether VH should be adjusted. Compliance voltage generator block 76 includes circuitry for boosting a power supply voltage such as the battery voltage, Vbat, to a proper level for VH. Such boost circuitry (some of which may be located off chip) can include an inductor-based boost converter or a capacitor-based charge pump, which are described in detail in U.S. Patent Application Publication 2010/0211132.

Clock generation block 74 can be used to generate a clock for the ASIC 160 and communication on the bus 192. Clock generation block 74 may receive an oscillating signal from an off-chip crystal oscillator 56, or may comprise other forms of clock circuitry located completely on chip, such as a ring oscillator. U.S. Patent Application Publication 2014/0266375 discloses another on-chip circuit that can be used to generate a clock signal on the ASIC 160.

Master/slave control block 86 can be used to inform the ASIC 160 whether it is to be used as a master ASIC or as a slave ASIC (e.g., 160 or 160' in FIG. 2A), which may be bond programmed at M/S terminal 61. For example, M/S terminal may be connected to a power supply voltage (e.g., Vbat) to inform ASIC 160 that it will operate as a master ASIC, or to ground to inform that it will operate as a slave 160', in which case certain function blocks will be disabled, as the above-cited references explain.

Nonvolatile memory (NOVO) block 78 caches any relevant data in the system (such as log data). Additional memory (not shown) can also be provided off-chip via a serial interface block 84.

ASIC 160 further includes a stimulation circuitry block 170, which includes circuitry for receiving and storing stimulation parameters from the microcontroller block 150 via bus 192. Stimulation parameters define the shape and timing of stimulation pulses to be formed at the electrodes, and can include parameters such as which electrodes E1-E16 will be active; whether those active electrodes are to act as anodes that source current to a patient's tissue, or cathodes that sink current from the tissue; and the amplitude (A), duration (D), and frequency (f) of the pulses. Amplitude may comprise a voltage or current amplitude. Such stimulation parameters may be stored in registers in the stimulation circuitry block 170. See, e.g., U.S. Patent Application Publications 2013/0289661; 2013/0184794.

Simulation circuitry block 170 also includes a Digital-to-Analog Converter (DAC) 172 for receiving the stimulation parameters from the registers and for forming the prescribed pulses at the selected electrodes. FIG. 3 shows a simple example of DAC circuitry 172 as used to provide a current pulse between selected electrodes E1 and E2 and through a patient's tissue, Rt. DAC circuitry 172 as shown comprises two portions, denoted as PDAC 172p and NDAC 172n. These portions of DAC circuitry 172 are so named because of the polarity of the transistors used to build them and the polarity of the currents they provide. Thus, PDAC 172p is formed from P-channel transistors and is used to source a current +I to the patient's tissue Rt via a selected electrode E1 operating as an anode. NDAC 172n is formed of N-channel transistors and is used to sink current −I from the patient's tissue via a selected electrode E2. It is important that current sourced to the tissue at any given time equal that sunk from the tissue to prevent charge from building in the tissue, although more than one anode electrode and more than one cathode electrode may be operable at a given time.

PDAC 172p and NDAC 172n receive digital control signals from the registers in the stimulation circuitry block 170, denoted <Pstim> and <Nstim> respectively, to generate the prescribed pulses with the prescribed timing. In the example shown, PDAC 172p and NDAC 172n comprise current sources, and in particular include current-mirrored transistors for mirroring (amplifying) a reference current Iref to produce pulses with an amplitude, A. PDAC 172p and NDAC 172n could however also comprise constant voltage sources. Control signals <Pstim> and <Nstim> also prescribe the timing of the pulses, including their duration (D) and frequency (f), as shown in the waveforms generated at the selected electrodes. The PDAC 172p and NDAC 172n along with the intervening tissue Rt complete a circuit between a power supply VH—the compliance voltage as already introduced—and ground. As noted earlier, the compliance voltage VH is adjustable to an optimal level at compliance voltage generator block 76 (FIG. 2B) to ensure that current pulses of a prescribed amplitude can be produced without unnecessarily wasting IPG power.

The DAC circuitry 172 (PDAC 172p and NDAC 172n) may be dedicated at each of the electrodes, and thus may be activated only when its associated electrode is selected as an anode or cathode. See, e.g., U.S. Pat. No. 6,181,969. Alternatively, the current produced by one or more DACs (or one or more current sources within a DAC) may be distributed to a selected electrode by a switch matrix (not shown), in which case optional control signals <Psel> and <Nsel> would be used to control the switch matrix and establish the connection between the selected electrode and the PDAC 172p or NDAC 172n. See, e.g., U.S. Pat. No. 8,606,362. DAC circuitry 172 may also use a combination of these dedicated and distributed approaches. See, e.g., U.S. Pat. No. 8,620,436.

In the example waveform shown, the pulses provided at the electrodes are biphasic, meaning that each pulse comprises a first phase 94a of a first polarity, followed by a second phase 94b of an opposite polarity. This is useful as a means of active recovery of charge that may build up on the DC-blocking capacitors 55. Thus, while charge will build up on the capacitors 55 during the first pulse phase 94a, the second pulse phase 94b will actively recover that charge, particularly if the total amount of charge is equal in each phase (i.e., of the area under the first and second pulse phases are equal). Recovery of excess charge on the DC-blocking capacitors 55 is important to ensure that the DAC circuitry 172 will operate as intended: if the charge/voltage across the DC-blocking capacitors 55 is not zero at the end of each pulse, remaining charge/voltage will skew formation of subsequent pulses, which may therefore not provide the prescribed amplitude.

While active recovery of charge using a biphasic pulse is beneficial, such active recovery may not be perfect, and hence some residual charge may remain on the DC-blocking capacitors 55 even after completion of the second phase 94b of the biphasic pulse. Thus, the art has recognized the utility of passive charge recovery. Passive charge recovery is implemented within the stimulation circuitry block 170, and includes use of passive recovery switches (transistors) 96, which are connected between the electrode nodes (E1'-E16') 61a and a common reference voltage. This voltage as shown may simply comprise the battery voltage, Vbat, but another reference voltage could also be used. Closing the passive recovery switches 96 during a time period 98 after the second pulse phase 94b couples the DC-blocking capacitors 55 in parallel between the reference voltage and the patient's tissue, Rt. Given the previous serial connection of the DC-blocking capacitors 55, this should normalize any remaining charge. See e.g., U.S. Provisional Patent Application Ser. No. 62/393,007, filed Sep. 10, 2016 (discussing advents related to passive recovery).

BRIEF DESCRIPTION OF THE DRAWINGS

FIGS. 1A-1C show an Implantable Pulse Generator (IPG), and the manner in which an electrode array is coupled to the IPG, in accordance with the prior art.

DETAILED DESCRIPTION

Figure 3:
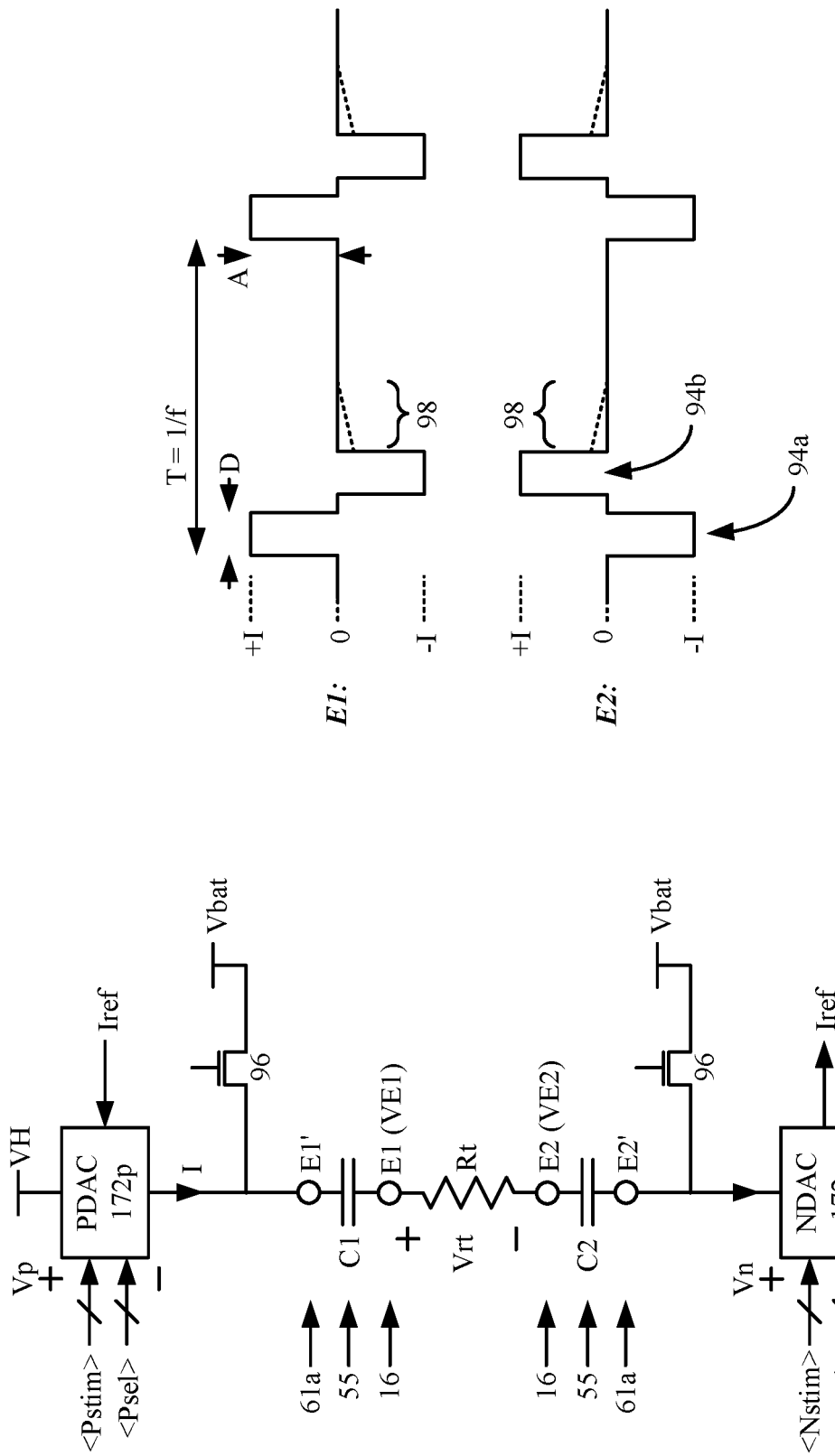
FIG. 3 shows aspects of the Digital-to-Analog converter (DACs) circuitry within the stimulation circuitry of the ASIC, and stimulation pulses formable thereby, in accordance with the prior art.
Figure 4:
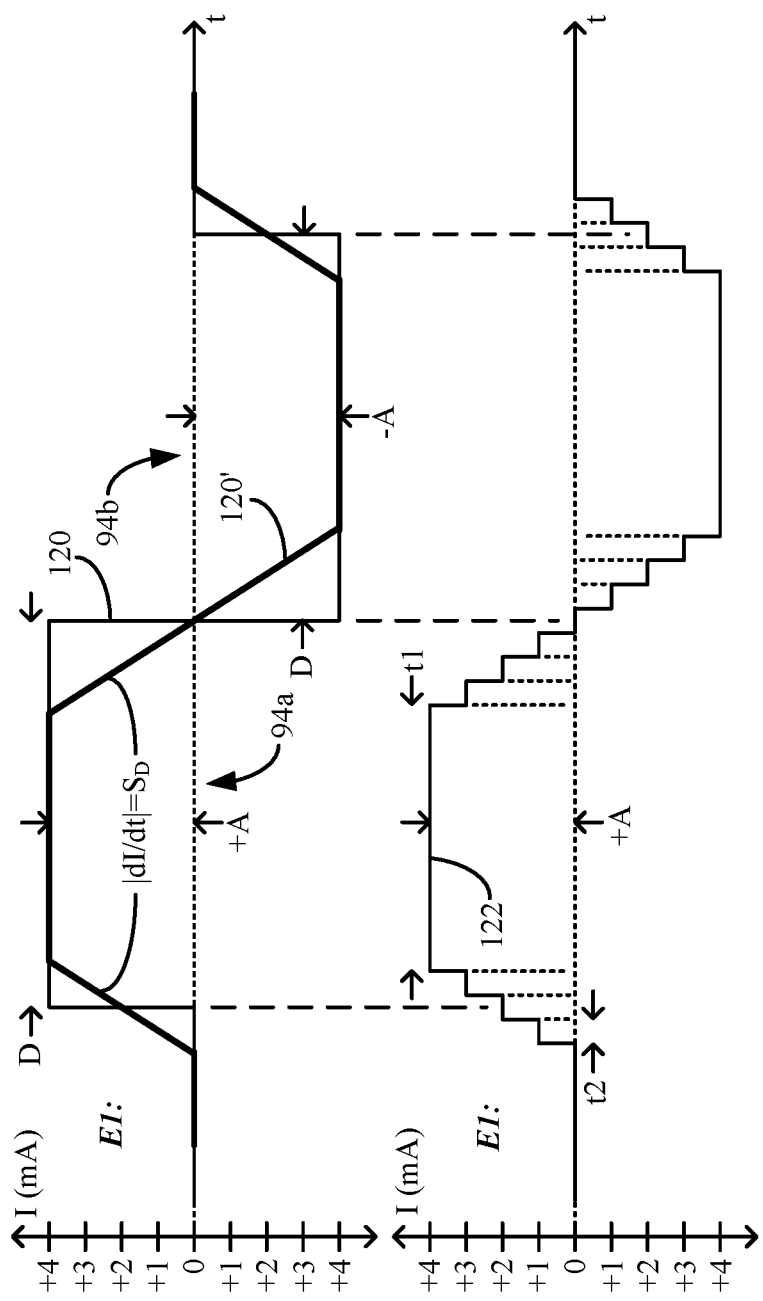
FIG. 4 shows a representation of a desired stimulation pulse having a slew rate, and the manner in which the desired slew rate is approximated by conventional DAC circuitry using a stair-stepped approach, in accordance with the prior art.

DAC circuitry 172 as described earlier in conjunction with FIG. 3 is particularly useful in providing pulses with phases of constant amplitudes (A) for constant durations (D) at a selected electrode 16. Such pulses may include biphasic pulses 120, one of which is shown in FIG. 4, and which as before includes a first pulse phase 94a and a second pulse phase 94b. Creation of such a pulse 120 is not difficult using the DAC circuitry 172 described earlier. Registers within the stimulation circuitry 170 store the amplitude A and duration D of the first pulse phase 94a, and direct a PDAC 172p via control signals <Pstim>(FIG. 3) to produce a positive (anodic) current at a selected electrode (e.g., E1) of the prescribed amplitude and duration. Producing the negative (cathodic) current during the second pulse phase 94b occurs similarly, although an NDAC 172n would now be controlled. If the PDAC 172 and NDAC 172 are not associated with (i.e., dedicated to) the selected electrode, control signals <Psel> and <Nsel>(FIG. 3) can be used to connect the PDAC 172p to that electrode, as explained earlier. Timers allow such pulse formation to occur periodically with a frequency f (FIG. 3).

A limitation of DAC circuitry 172 as described is that it can only define (per <Pstim>) a pulse with currents of constant amplitude (including zero), and therefore produces sharp transitions where the constant amplitudes changes (i.e., constant amplitude transitions when <Pstim> changes). This can make production of stimulation waveforms of more-complicated shapes difficult. Assume for example that it is desired to produce a pulse 120' similar to pulse 120, but with transitions between different amplitudes that are slewed, as shown in FIG. 4. That is, in desired pulse 120', the current ramps at pulse 120's transitions at a controlled slew rate or slope ($|dI/dt|=S_D$), instead of changing essentially instantaneously at sharp steps (where the slew rate $|dI/dt|$ essentially infinite).

The ability to provide pulses with slewed amplitude transitions would be beneficial for a number of reasons. For one, slewed transitions would ease operation of the DAC circuitry 172 and render controlled issuance of stimulation pulses more reliable. Sharp transitions can cause relatively large voltages to appear essentially instantaneously across transistors in the DAC circuitry 172. This can cause ringing, leading to unwanted oscillations and overshoot in the transistors, and ultimately in the currents the DAC circuitry 172 produces. Ringing can impact the reliability of the transistors, or require the transistors to be made from more resilient, complicated, and expensive designs. Further, ringing is particularly detrimental to pulses formed with shorter durations and higher frequencies, because ringing would constitute a significant deviation from such small-time-scale signals. It would therefore be desirable to control the current producible by the DAC circuitry 172 to ramp at amplitude transitions to some degree, which would reduce these unwanted effects.

Nonetheless, DAC circuitry 172 as described cannot produce pulse 120' with slewed transitions, because it can only provide a prescribed constant current for a prescribed duration. DAC circuitry 172 can therefore at best only approximate the slew rate $S_D$ that is desired in pulse 120' by forming a pulse 122 with a number of sharp steps approximating stair steps, as shown at the bottom in FIG. 4. As shown, each transition comprises a number of steps, each of a small duration t2, and with increasing or decreasing constant amplitudes depending whether the pulse 122 is increasing or decreasing. In total, and as shown in dotted lines, stepped pulse 122 is formed by DAC circuitry 172 as fifteen individual constant current pulse phases—thirteen of duration t2 at the stepped transitions (including zero), and two of duration t1 at maximum amplitudes +A and −A. Each of these individual pulse phases must be defined in registers in the stimulation circuitry 170 and sent to the DAC circuitry 172 for implementation. Not only does this approach not perfectly model desired slewed pulse 120', it is also memory intensive, because registers for fifteen pulse phases are needed to create a single biphasic pulse. Further, transitions between each of the fifteen pulse phases require transistors in the DAC circuitry 172 to switch, which requires additional power. If smaller duration steps were used in pulse 122 to better approximate the shape of slewed pulse 120', even further memory would be required and even further power would be consumed.

The inventors here provide a solution in the form of improved DAC circuitry that is programmable to set a controlled slew rate for pulses that are otherwise defined as having sharp transitions. In this manner, the improved DAC circuit is both simple and flexible. For example, when producing a biphasic pulse as described above, the constant amplitude and duration of first and second pulses phases can be defined and stored in traditional fashion. Slew rate control signals control a slew rate DAC, which prescribes a slew rate that will appear at sharp transitions of the biphasic pulses, i.e., at the beginning of the first phase, at the transition from the first to the second phase, and at the end of the second phase. The prescribed slew rate can vary with the duration or frequency of the pulses, such that lower slew rates are used with longer durations and/or lower frequencies, and higher slew rates are used with shorter durations and/or higher frequencies.

Figure 5:
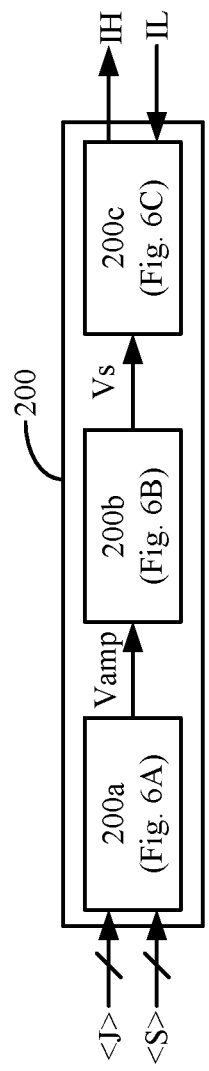
FIG. 5 shows improved master DAC circuitry able to form stimulation pulses with a programmable slew rate, in accordance with an example of the invention.
Figure 6A:
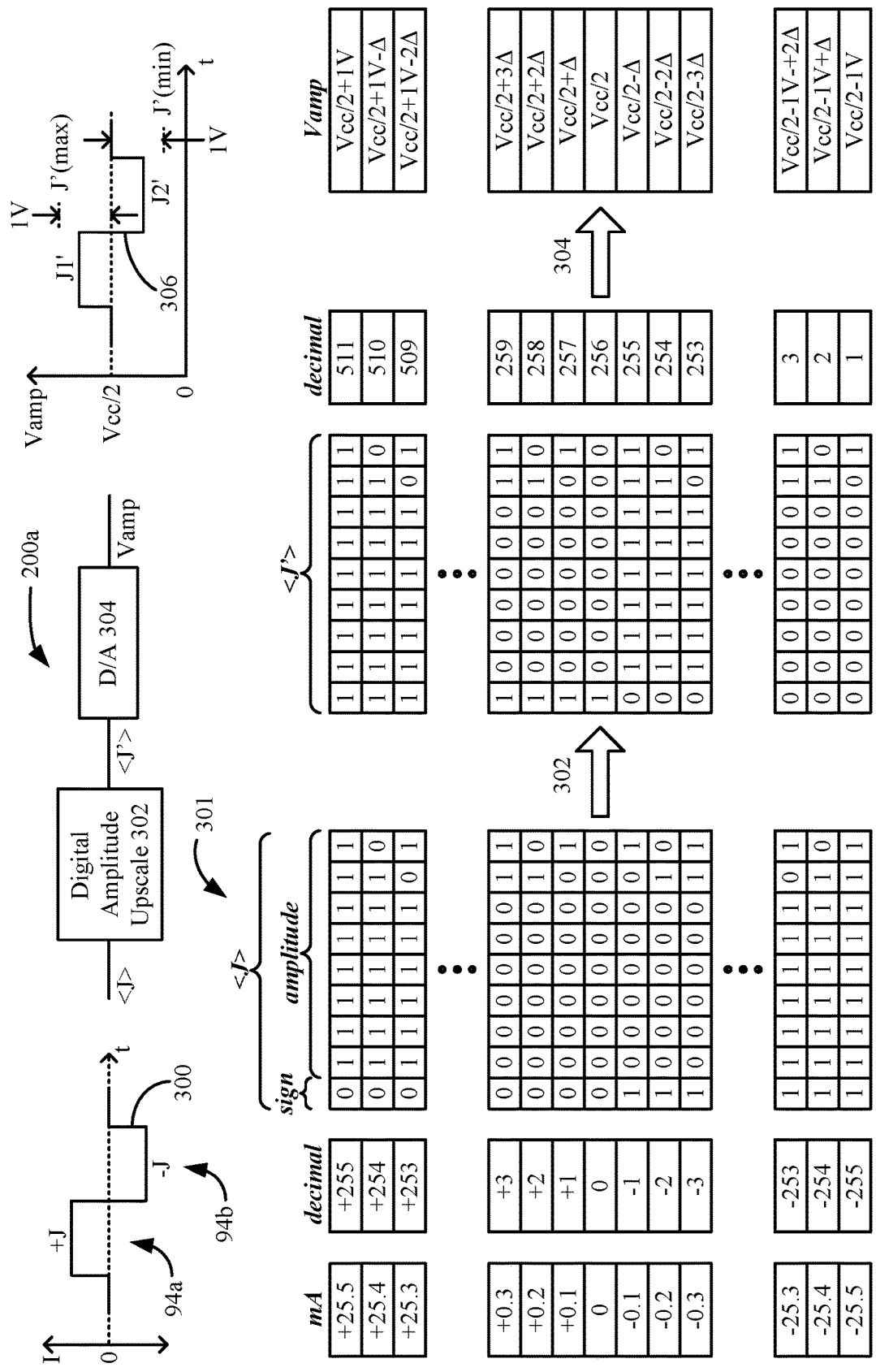
FIGS. 6A-6C show various stages of the master DAC circuity, including a DAVC stage (FIG. 6A), a slew stage (FIG. 6B), and a current generation stage (FIG. 6C), in accordance with an example of the invention.
Figure 6B:
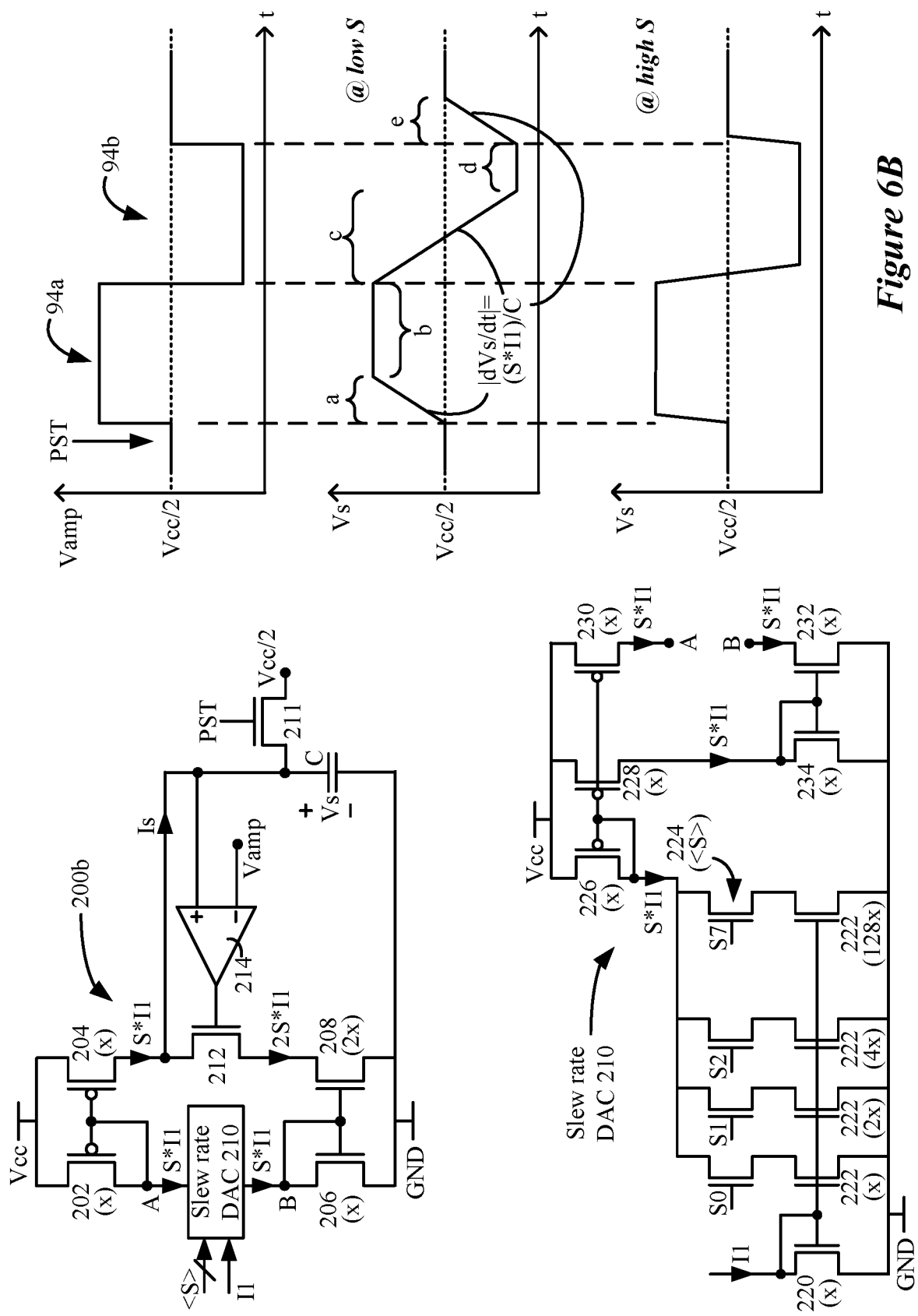
Figure 6C:
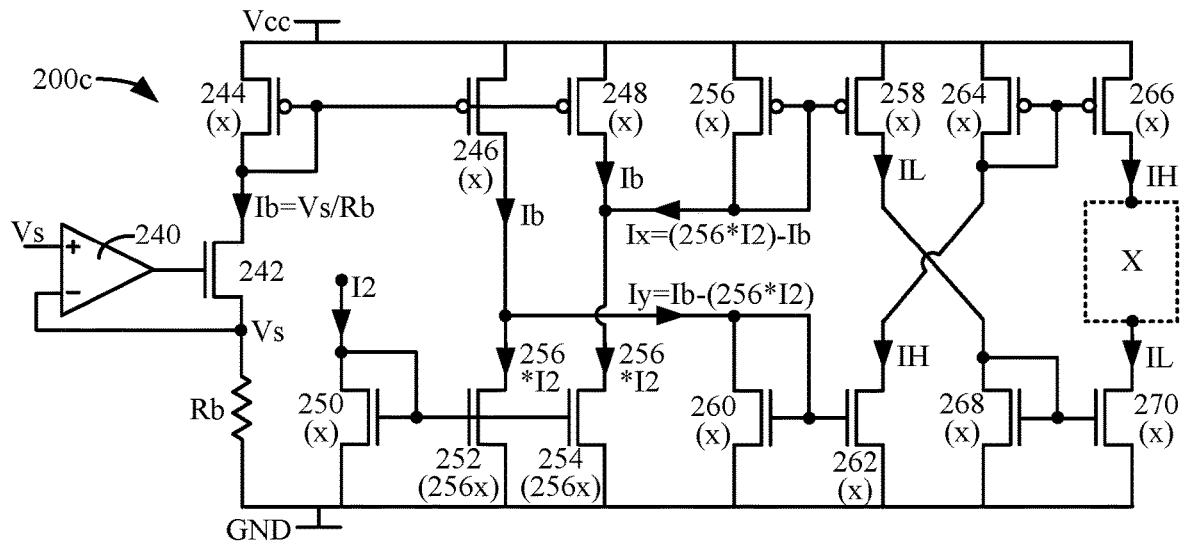
Figure 6C:
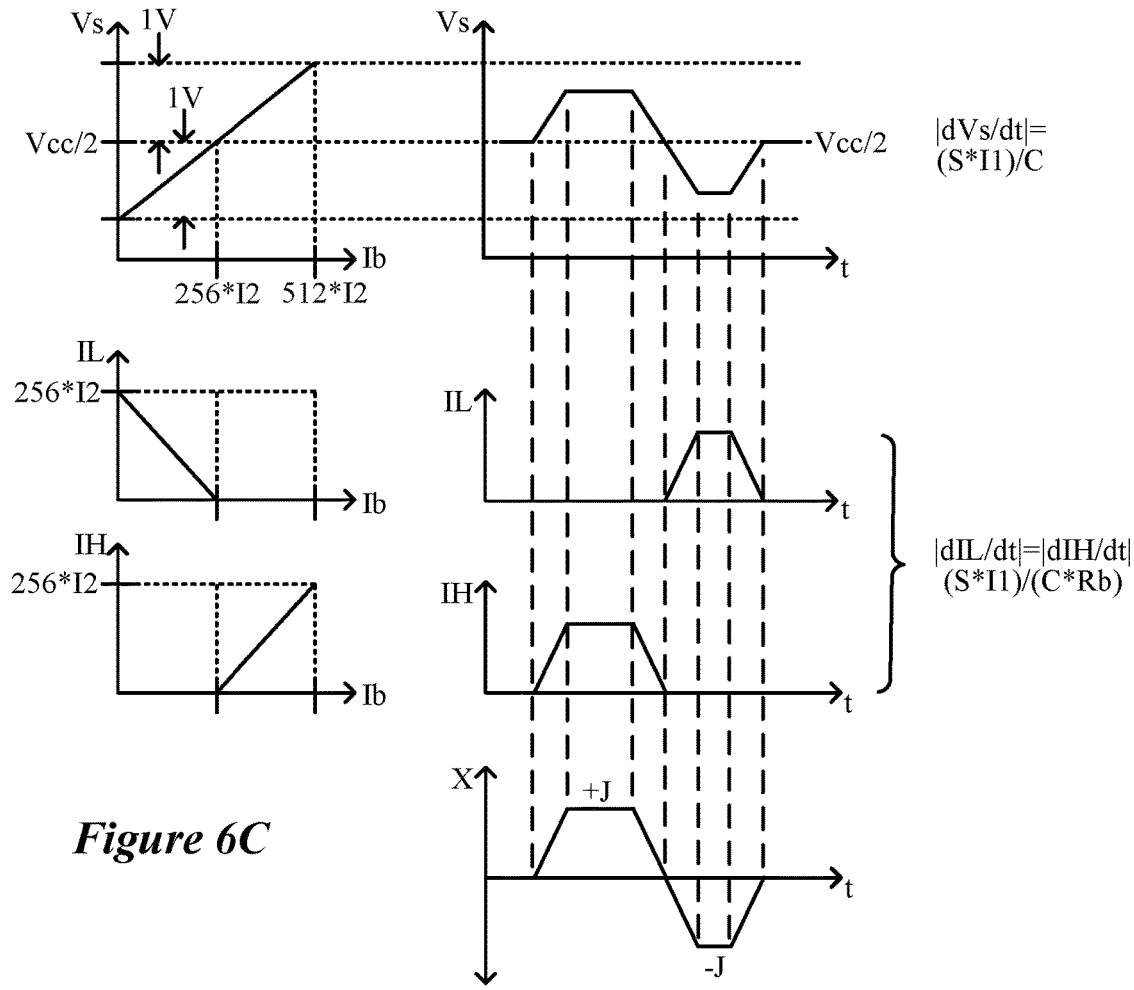

FIG. 5 shows an example of improved DAC circuitry 200, which comprises connected stages 200a, 200b, and 200c, examples of which are each individually illustrated in FIGS. 6A, 6B, and 6C respectively. The improved DAC circuitry 200 is referred to herein as a "master DAC 200" to differentiate it from the "slew rate DAC" it contains, as explained further below.

FIG. 6A show the digital-to-analog voltage converter (DAVC) circuitry stage 200a of the master DAC 200 in which a digitally-defined pulse 300 is converted to an analog voltage appropriate for subsequent processing. In this example, the digitally-defined pulse 300 again comprises a biphasic pulse 300 with two phases, although this is strictly one example. The master DAC circuitry 200 can process a digitally-defined pulse 300 of any shape and with any number of positive or negative phases, including a single phase.

Figure 2A:
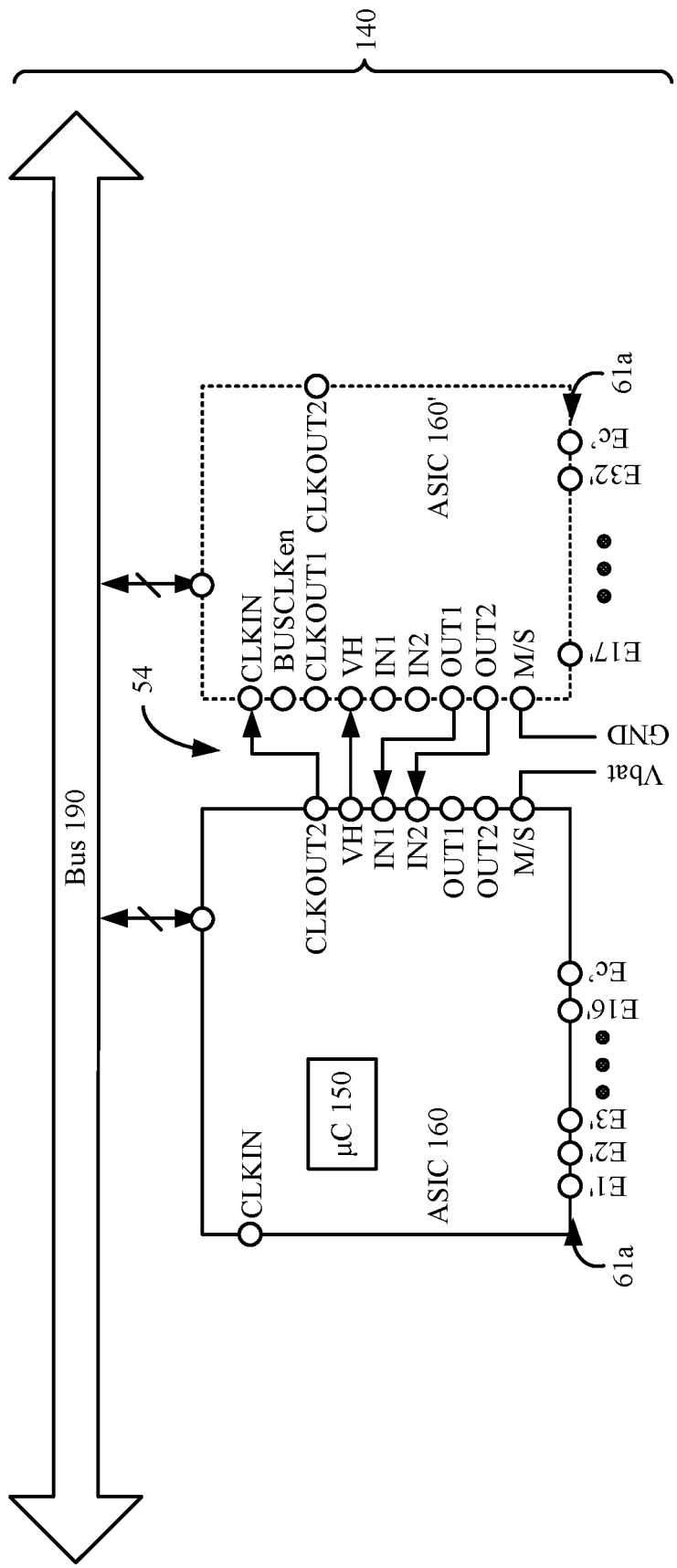
FIG. 2A shows an architecture for an IPG utilizing an Application Specific Integrated Circuit (ASIC) including an embedded microcontroller.
Figure 2B:
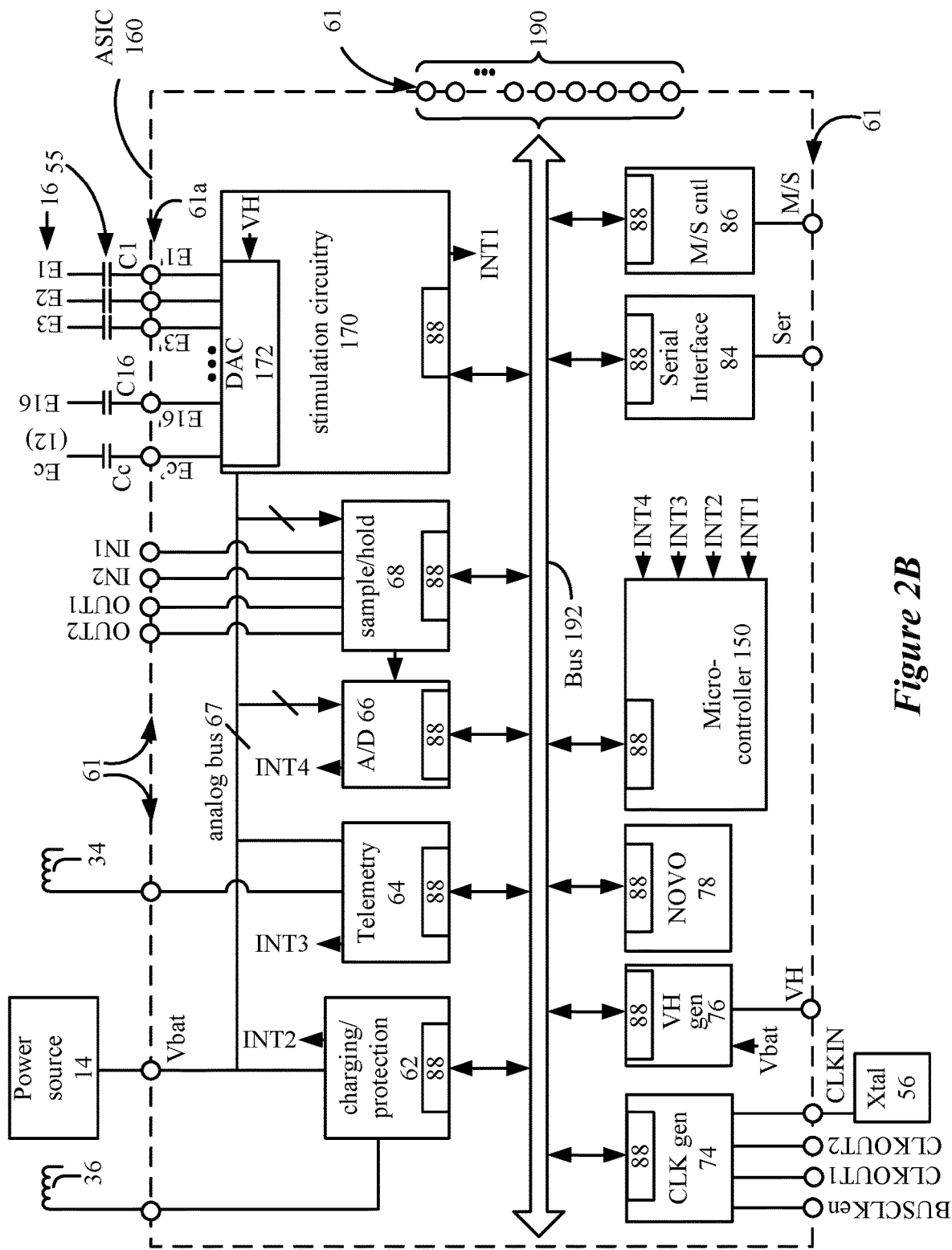
FIG. 2B shows functional circuitry blocks within the ASIC.

In the example shown, the first and second pulse phases 94a and 94b of pulse 300 are digitally defined as having constant current amplitudes +J and −J of certain durations, although their durations are not further discussed. The manner in which pulse 300's amplitudes can be digitally defined is shown at 301, and comprises nine digital bits provided by control signals <J>. Eight bits define the amplitude, while one bit defines the sign (positive or negative). The eight amplitude bits and the sign bit define currents that range in units from −255 to +255, corresponding in this example to currents from −25.5 mA to 25.5 mA. In other words, the digital amplitude bits allow the current of pulse 300 to be changed in units of 0.1 mA. Control signals <J> can be provided by registers in the stimulation circuitry 170 (FIG. 2B).

It is useful to translate the digitally-defined current amplitudes to positive values, and this occurs at a digital amplitude upscaling block 302, which translates control signals <J> into new digital control signals <J'>. Stated simply, block 302 adds 256 to each current (<J'>=<J>+256), so that <J'> now ranges in units from 1 to 511. Note that <J'> includes the same number of bits (nine) as did <J>, but lacks a sign bit as all values for <J'> are positive.

Positive digital control signals <J'> are then converted to a positive analog voltage, Vamp 306, by a digital-to-analog voltage converter (D/A) 304. It is preferred for headroom purposes to define the range of Vamp to fit comfortably within a power supply voltage (Vcc) of the ASIC 160 and to be centered at a reference voltage such as Vcc/2. For example, if Vcc=3.2V, D/A 304 may cause Vamp to range from 0.6V (at J'(min)=1, when J=−255) to 2.6V (at J'(max) =511, when J=+255) in 510 voltage increments (A). Notice that Vamp mimics the shape and relative amplitude of digitally-defined current pulse 300, with Vamp having a voltage amplitude J1' during the first pulse phase 94a, and J2' during the second pulse phase 94b.

Vamp in one example is provided to a slew rate stage 200b of the master DAC 200, which is shown in FIG. 6B. This stage 200b produces an analog voltage Vs that adds a programmable slew rate (|dVs/dt|) to the otherwise sharp transitions of Vamp. Slew rate programmability is provided by a slew rate DAC 210, an example of which is shown at the bottom of FIG. 6B.

Slew rate DAC 210 receives a reference current I1 and a plurality of slew rate control signals <S>. Slew rate control signals <S> can be provided by registers in the stimulation circuitry 170 (FIG. 2B). Each slew rate control signal (S0-S7) is sent to a control transistor 224, each of which is in turn connected to a transistor 222 to form a plurality of legs. Transistor 220 mirrors a reference current I1 to transistors 222, as they are connected in a traditional current mirror configuration in which I1 is provided to the drain of transistor 220 and to a common gate of transistors 220 and 222, as is well known. Because each current mirror transistor 222 has a different width (x) relative to transistor 220, each leg of the slew rate DAC 210 will carry a scaled amount of the mirrored reference current. For example, the leg controlled by S0 will carry I1, because the width (x) of its transistor 222 equals the width (x) of transistor 220; S1 will carry 2*I1, because its transistor 222 (2x) is twice the width of transistor 220. S2 will carry 4*I1, and so on in binary fashion. While transistors 222 may be made of different widths, transistors 222 may each also be formed of different numbers of transistors of width x connected in parallel, which achieves the same scaling of reference current I1, as is well known.

The currents from the various legs sum to produce a current S*I1 through transistor 226, which can vary from I1 to 255*I1 in increments of I1 depending on which control signals <S> are asserted. It should be noted that the number of control signals <S> and the extent to which each transistor 222 amplifies the reference current I1 can be varied. Current S*I1 is in turn mirrored to transistors 228 and 230, and transistor 234 mirrors S*I1 to transistor 232. The result is that transistor 230 sources current S*I1 to node A, while transistor 232 sinks current S*I1 from node B.

Returning to the top of FIG. 6B, current S*I1 provided by the slew rate DAC 210 is mirrored from transistor 202 to transistor 204. Current S*I1 is also mirrored by transistor 206 to transistor 208, although because transistor 208 has twice the width (2x) of transistor 206 (x), transistor 208 can carry 2S*I1, although as explained further below, the actual current through transistor 208 will be controlled by the extent to which transistor 212 is turned on by operational amplifier (op amp) 214. Transistor 212 is connected in series between transistors 204 and 208, which as just noted is controlled by op amp 214. Vamp as output from the DAVC stage 200a (FIG. 6A) is provided to the inverting input of op amp 214. The non-inverting input of op amp 214 is connected across a capacitor C, which capacitor receives a current Is. A transistor 211 can be used if necessary to preset the voltage across the capacitor, Vs, to Vcc/2 prior to processing a pulse upon assertion of a preset signal, PST.

So connected, slew rate stage 200b will produce a voltage across the capacitor C, Vs, that tracks Vamp, but that slews at the transitions at a rate that varies proportionally with S as set by control signals <S>. This is described with reference to different regions 'a'-'e' depicted in waveform Vs at the right in FIG. 6B.

At the beginning of the first pulse phase 94a, Vamp's amplitude is J1' (FIG. 6A), which is above Vcc2. Because Vs across the capacitor C is preferably preset to Vcc/2 (PST), op amp 214 outputs a '0', and transistor 212 is off. This allows a current of magnitude S*I1 to flow from transistor 204 to the capacitor C (i.e., Is=S*I1), which charges capacitor C and causes Vs to rise during region 'a'. The slew rate of this rise (dVs/dt) comprises the current (S*I1) divided by the capacitance (C). Assuming I1 and C are set to sensible known values, the slew rate of Vs is thus proportional to the value of S set by control signals <S> in the slew rate DAC 210.

At the end of region 'a', Vs has increased to equal Vamp. At this point, the feedback provided by op amp 214 and transistor 212 will force Vs to equal Vamp. More specifically, op amp 214 will turn transistor 212 on to an extent necessary to pass the S*I1 current from transistor 204 to transistor 208, and thus Is=0. As a result, during period 'b', Vs equals Vamp.

At the end of region 'b', that is, at the beginning of the second pulse phase 94b, Vamp's amplitude is J2', which is below Vcc/2. This causes op amp 214 to output a '1', thus fully turning on transistor 212, which allows the full amount of current 2S*I1 to sink through transistor 208. The net effect (summing the current S*I1 provided by transistor 204 and −2S*I provided by transistor 208) is that the magnitude of current Is now equals −S*I1, which draws charge off of capacitor C. This causes Vs to decrease during region 'c', and because the absolute value of the current is the same as during period 'a', the slew rate (−(S*I1)/C)) is also the same (dVs/dt=−(S*I1)/C)), albeit negative.

At the end of region 'c', Vs once again equals Vamp, and again Vs is forced by op amp 214 and transistor 212 to equal Vamp during region 'd'. At the end of region 'd', which in this example corresponds to the end of the second pulse phase 94b, Vamp is equal to Vcc/2 (meaning that the actual prescribed current J is equal to zero; see FIG. 6A). Because this is higher than Vs, capacitor C is again charged with the prescribed slew rate during region 'e' (dVs/dt=(S*I1)/C)), similar to what occurred during region 'a'. Eventually, Vs will charge to Vcc/2, which equals Vamp. If necessary, Vs can be explicitly set to Vcc/2 (via PST) prior to issuance of a next pulse.

As already noted, the value of S as set by control signals <S> proportionately varies the slew rate of the transitions of Vs, and FIG. 6B illustrates this by showing Vs as produced using relatively low (middle graph) and high (bottom graph) values for S. As alluded to earlier, relatively high values for slew rate S are especially desirable if the duration of the pulses is short, and/or if the frequency of pulses is relatively high, because a high slew rate renders a high slope to the slew which will less affect the shape of such small-time-scale pulses.

Vs is then sent to a current generation stage 200c of the master DAC 200, as shown in FIG. 6C. As will be explained, this stage 200c allow Vs as slewed to be converted into a source current IH that scales with Vs relative to Vcc/2 when Vs is greater than Vcc/2, and converted into a sink current IL that scales with Vs relative to Vcc/2 when Vs is less than Vcc/2.

Vs is presented to a non-inverting input of an op amp 240 that controls a transistor 242. Due to the feedback provided by the inverting input, the current through transistor 242 will equal a bias current Ib=Vs/Rb. Ib is mirrored from transistor 244 to transistors 246 and 248.

A reference current I2 is provided to transistor 250, which is mirrored to, and preferably amplified by, transistors 252 and 254. In the example shown, transistor 252 and 254 are 256 times the width x of transistor 250 (or each comprise 256 transistors of width x connected in parallel), and so transistors 252 and 254 will each carry 256*I2. A scalar other than 256 could be chosen for amplification of I2. Reference current I2 can equal the reference current I1 used in the slew rate DAC 201 of FIG. 6B, but this isn't strictly necessary.

It is preferred that bias current Ib equal 256*I2 when Vs is equal to Vcc/2. This can be achieved by appropriate selection of resistor Rb (as Vcc/(512*I2)).

Providing current Ib from transistors 246 and 248 and current 256*I2 from transistors 252 and 254 creates difference currents Ix and Iy, with Ix=(256*I2)−Ib and Iy=Ib−(256*I2). Transistor 256 mirrors Ix to transistor 258, and transistor 260 mirrors Iy to transistor 262.

When Vs is greater than Vcc/2, Ib is larger than 256*I2. Iy is thus positive, and transistor 260 will thus mirror Iy to transistor 262 to create current IH. If desired, IH can be provided to transistor 264 and mirrored to transistor 266 as shown. Notice that as Vs increases, bias current Ib will also increase, and hence IH will increase (proportionately to Vs−Vcc/2). Ix, by contrast, is negative, and therefore will short to Vcc through transistor 256. Transistor 256 will thus mirror no current to transistor 258, and IL will be equal to zero. The graphs in the left column of FIG. 6C help to show these relationships.

By contrast, when Vs is less than Vcc/2, Ib is smaller than 256*I2. Ix is thus positive, and transistor 256 will thus mirror Ix to transistor 258 to create current IL. If desired, IL can be provided to transistor 268 and mirrored to transistor 270 as shown. Notice that as Vs decreases, bias current Ib will also decrease, and IL will increase (proportionally to Vcc/2−Vs). Iy, by contrast, is negative, and therefore will short to ground through transistor 260. Transistor 260 will thus mirror no current to transistor 262, and IH will be equal to zero.

The graphs in the right column of FIG. 6C illustrate the overall effect of current generation stage 200c for slewed input pulse, Vs. When Vs is above Vcc/2, IH will issue; when Vs is below Vcc/2, IL will issue. During time periods when Vs is slewed, IH and IL will also be slewed. The slew rate of IH and IL will, like Vs, vary proportionately with the slew S set by control signals <S> in the slew rate DAC 210. However, the slew rate of IH and IL will also be affected by the conversion of Vs to Ib, such that the slew rate of IH and IL will also vary depending on Rb-i.e., $|dIL/dt|=|dIH/dt|=(S*I1)/(C*Rb)$.

Current generation stage 200c, or master DAC 200 more generally, thus creates currents IH and IL that can respectively source (positive) current to and sink (negative) current from a node X. The current producible at node X can comprise the original digitally-defined pulse current pulse 300 (FIG. 6A) with the proper amplitudes (+J and −J), but with transitions slewed proportionally by S as prescribed by control signals <S>(FIG. 6B). For example, if it is assumed that reference current I2=0.1 mA in stage 200c, then the current at node X will vary from a minimum of −25.5 mA (at J=−255, J'=1, Vamp=Vcc/2−1V); to zero (at J=0, J'=256, Vamp=Vcc/2); and to a maximum of +25.5 mA (at J=+255, J'=511, Vamp=Vcc/2+1V), which equal the current amplitudes specified for the digitally-defined current pulse 300 of FIG. 6A.

Note that IH and IL are produced at different times depending whether Vs as slewed is greater than or less then Vcc/2. Nonetheless, the current generation stage 200c allows for a smooth, slewed transition between positive and negative current at node X.

Figure 7:
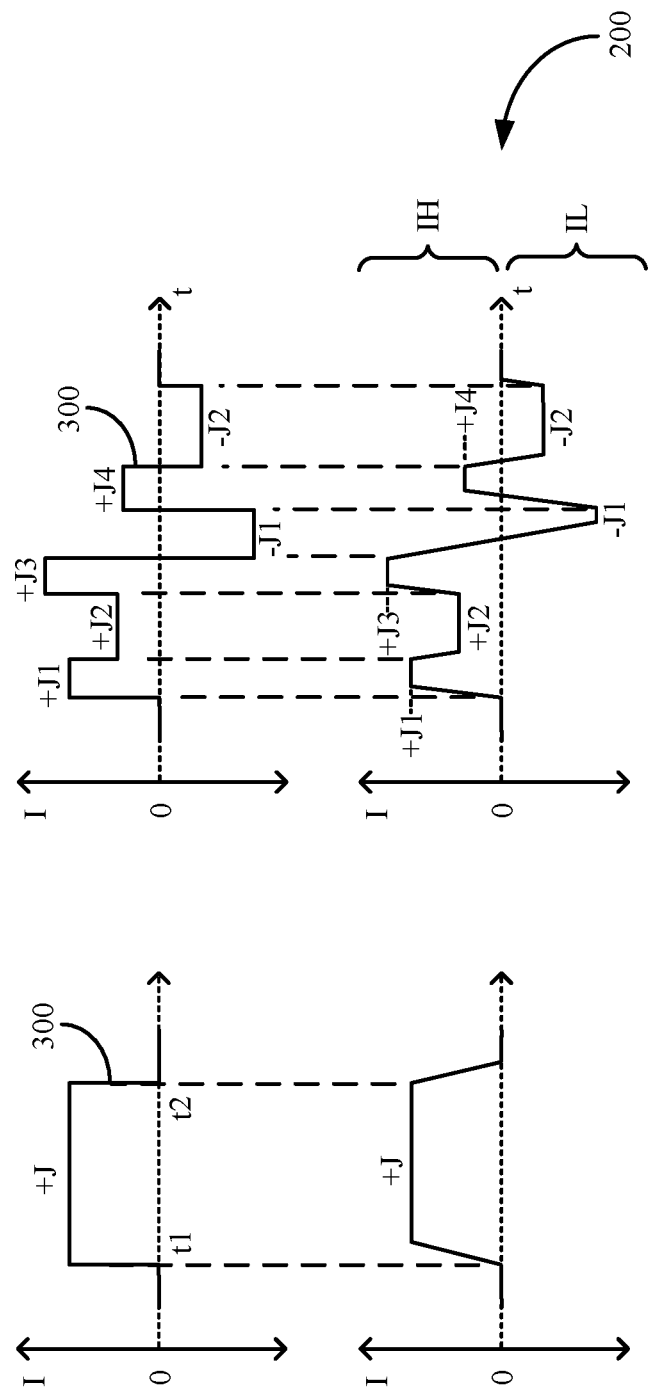
FIG. 7 shows operation of the master DAC circuitry to transform different pulses digitally defined with one or more constant amplitudes to pulses that are programmably slewed at transitions of those amplitudes, in accordance with examples of the invention.

FIG. 7 shows examples of other digitally-defined pulses 300 of constant amplitude(s) that can be processed by master DAC circuit 200 to provide a slew at points in time in which the amplitude is otherwise prescribed to change instantaneously at a step. The left shows a single phase pulse of a single constant amplitude J+, in which the pulse is defined to change instantaneously from 0 to +J at t1, and back to zero at t2. As shown, master DAC circuitry 200 changes this pulse into a current pulse that starts slewing upward proportionally with S at t1, then tracks +J, and then starts slewing downward proportionally with S at t2. In this instance, because pulse 300 is defined as being always positive, the current output by master DAC 200 is provided solely by IH. The right of FIG. 7 shows a more-complicated digitally-defined pulse comprising several phases each with a different constant amplitude, some positive (+J1 to +J4), and some negative (−J1, −J2). Nonetheless, again master DAC 200 changes this pulse so that the output current pulse begins to slew proportionally with S either upwards or downward at the otherwise instantaneous transitions between the different constant amplitudes. As described earlier, positive phases are produced by IH while negative phases are produced by IL.

Figure 8B:
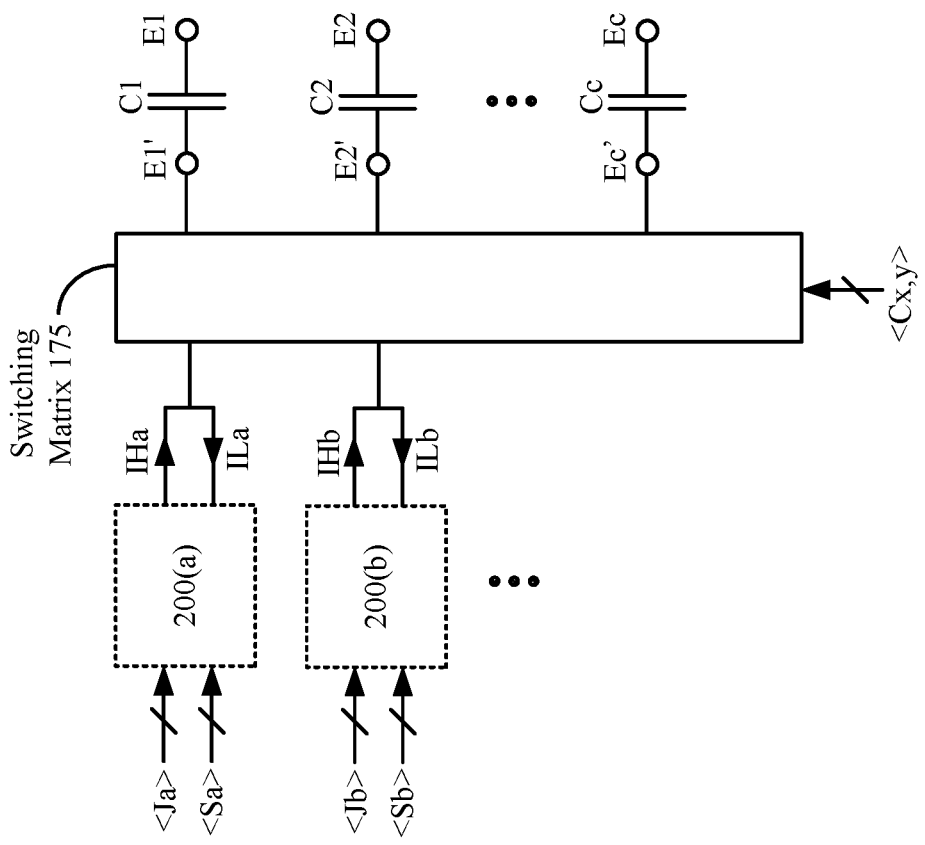
FIGS. 8A and 8B show different manners in which the master DAC can be used to provide stimulation pulses to electrode nodes of an IPG with the programmable slew, including use of dedicated master DACs at each electrode node (FIG. 7A), and connection of any electrode node to one or more master DACs using a switch matrix, in accordance with examples of the invention.
Figure 8A:
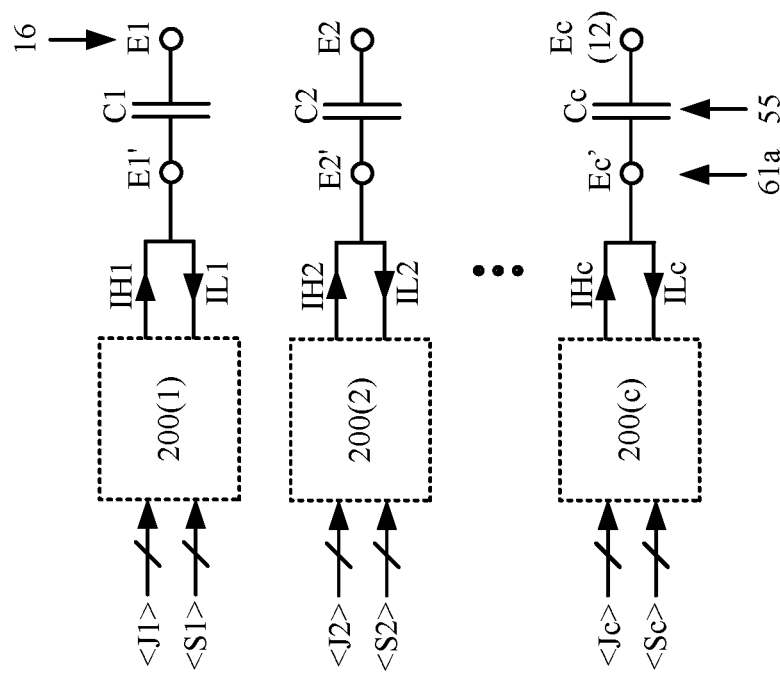

FIGS. 8A and 8B show different manners in which master DAC circuitry 200 can be used to provide stimulation to the electrode nodes 61a, and ultimately to the electrodes 16 on the IPG lead(s) 18. The illustrated examples again assume that there are sixteen electrode nodes (E1'-E16') 61a that ultimately connect to the sixteen electrodes (E1-E16) 16 on the lead(s) 18, plus an additional electrode node 61a Ec' that ultimately connects to the IPG 10's conductive case 12. DC-blocking capacitors 55 are again preferably placed in series in each of the electrode output paths between the electrode nodes 61a and the electrodes 16. Passive recovery switches can be connected to each electrode node 61a as described earlier, but this is not shown.

In FIG. 8A, a master DAC (e.g., 200(1)) is dedicated (e.g., hardwired) to each electrode node 61a (e.g., El). Each master DAC 200 receives constant current amplitude control signals (e.g., <J1>) and slew rate control signals (e.g., <S1>) to set the slew rate at each change in amplitude, regardless whether the amplitude is positive or negative. In the example shown, IHx and ILx produced by each master DAC 200(*x*) are each shorted at their associated electrode node Ex'. Shorting IHx and ILx at the electrode node is not problematic, because, as discussed above, master DAC 200(*x*) will not issue IHx and ILx at the same time.

In FIG. 8B, one or more master DACs 200(*x*) are shareable between the electrodes nodes in a distributed fashion with the help of a switching matrix 175 and control signals <Cx,y>. For example, the currents produced by master DAC 200(*a*) can at a given time be connected to electrode node E3' upon assertion of an appropriate switch matrix control signal (e.g., Ca,3), while DAC 200(*b*) can likewise be connected to electrode node E2' (e.g., Cb,2). The number of master DACs 200(*x*) useable in an embodiment of FIG. 8B can be variable, and need not necessarily equal the number of electrode nodes 61a.

While master DAC 200 will produce currents at electrode nodes 61a at an appropriate slew rate, it is not necessary that currents IH and IL be of an amplitude that is appropriate for tissue stimulation, although they can be: for example, as explained earlier, reference current I2 as used in the current generation stage 200c may be set so that IH and IL, albeit slewed, are produced with an amplitude (e.g., J) specified earlier in the DAVC stage 200a.

Figure 9:
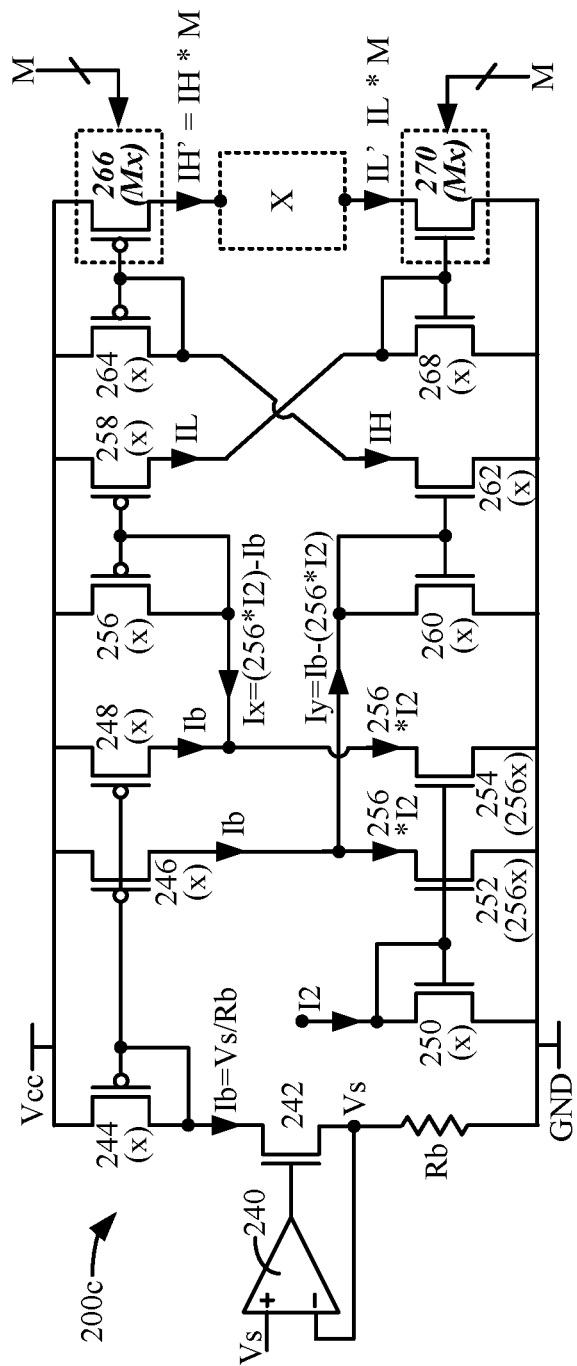
FIG. 9 shows how current produced by the master DAC can be controllably amplified before presentation to the electrode nodes, in accordance with an example of the invention.

In another example, the currents IH and IL may be lower than desired for tissue stimulation, but may be amplified before they are presented to an electrode node. FIG. 9 shows a simple example of such amplification. In this example, output driving stage comprising current-mirror transistors 266 and 270 respectively amplify currents IH and IL to IH' and IL' by setting the width or number (M) of these transistors. This can be controllable in accordance with amplification control signals <M>, which may operate similarly to control signals <S> in the slew rate DAC 210 (FIG. 6B) to include additional numbers of current-mirror-receiving transistors 266 and 270, hence amplifying IH and IL by M (i.e., IH'=IH*M; IL'=IL*M). This allows signal being processed prior to driving stage 266 and 270 to be of lower current (e.g., I2 and Ib can be reduced), which will draw less power from the IPG's battery 14. While IH' and IL' will slew over the time periods as IH and IL (and Vs), their actual slew rates will be affected by amplification factor M (i.e., $|dIL'/dt|=|dIH'/dt|=(S*M*I1)/(C*Rb)$).

Figure 10:
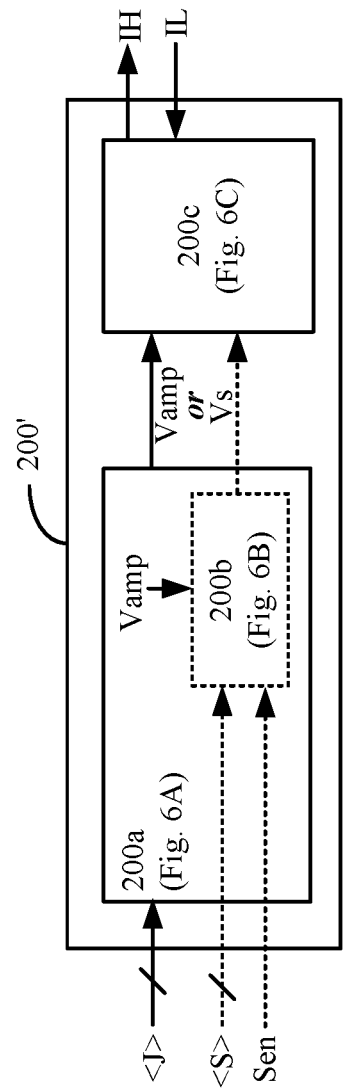
FIG. 10 shows an alternative embodiment for the master DAC not employing slew programmability.

While it is desirable to add a slew rate to pulses being processed by the master DAC 200, this isn't strictly necessary, as the inventors consider as additionally novel the current generation stage 200c's ability to convert an analog voltage representing a pulse into source and sink currents IH and IL. In this regard, slew rate stage 200b and use of slew rate control signals <S> are not strictly necessary, as shown in dotted lines in FIG. 10. Notice here that the optional slew rate stage 200b, if present, can be considered within the DAVC stage 200a. Normally, the DAVC stage 200a produces Vamp 306 (FIG. 6A), which comprises a non-slewed positive voltage representation of the digitally-defined pulse 300 centered at reference voltage Vcc/2. Because Vamp is divided into positive (>Vcc/2) and negative (<Vcc/2) portions similar to the capacitor slew voltage Vs (FIG. 6B), Vamp may be input directly into the current generation stage 200c (FIG. 6C, into op amp 240). This will cause the current generation stage 200c to form the necessary source and sink output currents IH and IL as described earlier. However, because Vamp is not slewed, IH and IL will likewise not be slewed, but this can be acceptable for neurostimulation.

If DAVC stage 200a includes slew rate stage 200b, whether the input digitally-defined pulse 300 will be slewed or not within the DAVC stage 200a can be selected via a slew rate enable signal, Sen. If Sen is enabled, slew rate control signals <S> are sent to the slew rate stage 200b within the DAVC stage 200a; Vs is then produced from Vamp with a slew rate proportional to S as set by <S>, and Vs is presented to current generation stage 200c to produce slewed versions of IL and IH with the prescribed slew. If Sen is not enabled, the slew rate stage 200b is disabled, and instead an un-slewed Vamp signal is provided to current generation stage 200c to produce IL and IH without slew.

While disclosed in the context of an implantable pulse generator, it should be noted that the improved master DAC circuitry could also be implemented in a non-implantable pulse generator, such as an External Trial Stimulator (ETS). See, e.g., U.S. Pat. No. 9,259,574 (describing an ETS).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A pulse generator, comprising:
   a plurality of electrode nodes, each electrode node configured to be coupled to an electrode to provide stimulation pulses to a patient's tissue; and
   digital-to-analog converter (DAC) circuitry configured to receive a plurality of digital amplitude signals defining an input pulse, wherein the plurality of digital amplitude signals prescribe at least one constant amplitude for the input pulse, and wherein the input pulse is characterized by constant amplitude transitions,
   wherein the DAC circuitry is further configured to receive a plurality of digital slew rate signals prescribing a slew rate, wherein DAC circuitry is further configured to form the input pulse as an output pulse at one of the plurality of electrode nodes that is slewed proportionally with the slew rate at the constant amplitude transitions.

2. The pulse generator of claim 1, wherein the at least one constant amplitude comprises a constant current amplitude, and wherein the output pulse comprises a current pulse.

3. The pulse generator of claim 1, wherein the input pulse comprises at least one constant positive amplitude and at least one constant negative amplitude.

4. The pulse generator of claim 1, wherein the DAC circuitry comprises a first stage comprising a digital-to-analog voltage converter circuitry (DAVC) configured to convert the plurality of digital amplitude signals to a positive analog voltage having the constant amplitude transitions.

5. The pulse generator of claim 4, wherein the DAC circuitry further comprises a second stage for receiving the positive analog voltage, wherein the second stage is configured to receive the plurality of digital slew rate signals and to form a second analog voltage proportional with the slew rate at the constant amplitude transitions in the positive analog voltage.

6. The pulse generator of claim 5, further comprising a third stage for receiving the second analog voltage and configured to convert the second analog voltage to the output pulse, wherein the output pulse is an output current pulse.

7. The pulse generator of claim 6, wherein the third stage forms the output current pulse using first and second currents.

8. The pulse generator of claim 7, wherein the first current forms positive portions of the output current pulse, and wherein the second current forms negative portions of the output current pulse.

9. The pulse generator of claim 1, wherein the DAC circuitry further comprises a capacitor, and wherein the plurality of digital slew rate signals set a magnitude of a current that charges and discharges the capacitor proportionally with the slew rate.

10. The pulse generator of claim 1, further comprising at least one implantable lead, wherein the electrodes are located on the at least one implantable lead.

11. A pulse generator, comprising:
    a plurality of electrode nodes, each electrode node configured to be coupled to an electrode to provide stimulation pulses to a patient's tissue; and
    digital-to-analog voltage converter (DAVC) circuitry configured to receive a plurality of digital amplitude signals defining an input pulse, wherein the DAVC circuitry is configured to form an analog voltage representative of the input pulse centered around a reference voltage; and
    a current generation stage for receiving the analog voltage, wherein the current generation stage comprises a first output configured to output a source current and a second output configured to output a sink current, wherein the source current is formed in response to positive amplitude portions of the analog voltage greater than the reference voltage, and wherein the sink current is formed in response to negative amplitude portions of the analog voltage less than the reference voltage.

12. The pulse generator of claim 11, wherein the source current scales with an amplitude of the positive amplitude portions relative to the reference voltage, and wherein the sink current scales with an amplitude of the negative amplitude portions relative to the reference voltage.

13. The pulse generator of claim 11, wherein the source current and the sink current are connected to one of the electrode nodes.

14. The pulse generator of claim 11, wherein the source current and the sink current are amplified before being connected to one of the electrode nodes.

15. The pulse generator of claim 14, wherein the source and sink currents are amplified in accordance with a plurality of amplification control signals.

16. The pulse generator of claim 11, wherein the DAVC circuitry is further configured to form transitions in the analog voltage as specified by the plurality of digital amplitude signals with a slew rate programmable in accordance with a plurality of digital slew rate control signals.

17. The pulse generator of claim 16, wherein the DAVC circuitry comprises a capacitor, wherein the digital slew rate signals set a magnitude of a current that charges and discharges the capacitor to form the transitions in the analog voltage proportional with the slew rate.

18. The pulse generator of claim 11, wherein the DAVC circuitry receives a slew rate enable signal configured to control whether transitions in the analog voltage as specified by the plurality of digital amplitude signals are formed with a programmable slew rate.

19. The pulse generator of claim 11, wherein the current generation stage is configured to form a bias current dependent on an amplitude of the analog voltage, wherein the current is compared to a reference current, wherein if the reference current is higher than the bias current, the source current is formed, and wherein if the reference current is less than the bias current, the sink current is formed.

20. The pulse generator of claim 11, further comprising at least one implantable lead, wherein the electrodes are located on the at least one implantable lead.

* * * * *